US008587660B2

(12) United States Patent
Mitra et al.

(10) Patent No.: US 8,587,660 B2
(45) Date of Patent: Nov. 19, 2013

(54) IMAGE RECORDING ASSEMBLIES AND COUPLING MECHANISMS FOR STATOR VANE INSPECTION

(75) Inventors: Chayan Mitra, Karnataka (IN); Munish Vishwas Inamdar, Karnataka (IN); Vinay Bhaskar Jammu, Karnataka (IN); Vinod Padmanabhan Kumar, Karnataka (IN); Kunal Ravindra Goray, Karnataka (IN); Achalesh Kumar Pandey, Greenville, SC (US); Ravi Yoganatha Babu, Karnataka (IN); Sheri George, Karnataka (IN); Bhasker Rao Keely, Karnataka (IN)

(73) Assignee: General Electric Company, Niskayuna, NY (US)

( * ) Notice: Subject to any disclaimer, the term of this patent is extended or adjusted under 35 U.S.C. 154(b) by 574 days.

(21) Appl. No.: 12/847,909

(22) Filed: Jul. 30, 2010

(65) Prior Publication Data
US 2012/0026306 A1    Feb. 2, 2012

(51) Int. Cl.
H04N 7/18    (2006.01)

(52) U.S. Cl.
USPC .......................................................... 348/158

(58) Field of Classification Search
USPC .................................................... 348/61–161
See application file for complete search history.

(56) References Cited

U.S. PATENT DOCUMENTS

| 4,686,972 | A |   | 8/1987  | Kurland |
| 4,777,949 | A |   | 10/1988 | Perlin |
| 4,882,667 | A |   | 11/1989 | Skegin |
| 4,991,068 | A |   | 2/1991  | Mickey |
| 5,164,826 | A | * | 11/1992 | Dailey ............................ 348/83 |
| 5,221,130 | A |   | 6/1993  | Satoh et al. |
| 5,511,567 | A |   | 4/1996  | Cefis |
| 5,542,762 | A | * | 8/1996  | Nakanishi et al. ............ 366/228 |
| 5,560,087 | A |   | 10/1996 | Marques |
| 5,580,159 | A |   | 12/1996 | Liu |
| 5,627,904 | A |   | 5/1997  | Yang et al. |
| 5,629,577 | A |   | 5/1997  | Polla et al. |
| 5,901,896 | A |   | 5/1999  | Gal |
| 5,946,127 | A | * | 8/1999  | Nagata ......................... 359/280 |
| 6,126,775 | A |   | 10/2000 | Cullen et al. |
| 6,414,458 | B1 |  | 7/2002  | Hatley et al. |
| 6,475,188 | B1 |  | 11/2002 | Baxter |
| 6,539,136 | B1 |  | 3/2003  | Dianov et al. |
| 6,592,043 | B1 |  | 7/2003  | Britton |
| 6,610,030 | B1 |  | 8/2003  | Baxter |

(Continued)

FOREIGN PATENT DOCUMENTS

| DE | 3312987 | 10/1984 |
| DE | 4126724 | 2/1993 |

(Continued)

OTHER PUBLICATIONS

U.S. Appl. No. 12/714,207, filed Feb. 26, 2010, Sheri George.

*Primary Examiner* — Joseph Ustaris
*Assistant Examiner* — Talha Nawaz
(74) *Attorney, Agent, or Firm* — Ann M. Agosti

(57) ABSTRACT

A system is disclosed that includes an image recording assembly for recording images of a stator vane of a compressor and a mechanism configured to magnetically couple the image recording assembly to a rotor blade of a compressor. Additional systems are provided that include image recording assemblies. Methods implementing the disclosed systems are also provided.

19 Claims, 20 Drawing Sheets

(56) References Cited

U.S. PATENT DOCUMENTS

| | | | |
|---|---|---|---|
| 6,637,737 B1 | 10/2003 | Beecherl et al. | |
| 7,004,957 B1 | 2/2006 | Dampney et al. | |
| 7,032,279 B2 | 4/2006 | McCarvill et al. | |
| 7,489,811 B2 | 2/2009 | Brummel et al. | |
| 7,689,030 B2 * | 3/2010 | Suh et al. | 382/149 |
| 8,196,305 B1 * | 6/2012 | Hansen et al. | 33/530 |
| 2002/0015557 A1 | 2/2002 | Yap et al. | |
| 2003/0228098 A1 | 12/2003 | Sidorovich | |
| 2004/0240078 A1 * | 12/2004 | Sekiyama | 359/726 |
| 2005/0056953 A1 | 3/2005 | Hofmann et al. | |
| 2005/0072135 A1 * | 4/2005 | Kormann | 56/500 |
| 2006/0078193 A1 * | 4/2006 | Brummel et al. | 382/152 |
| 2006/0234901 A1 | 10/2006 | Scheuing et al. | |
| 2006/0243302 A1 | 11/2006 | Mardero et al. | |
| 2006/0294254 A1 * | 12/2006 | Emerson et al. | 709/238 |
| 2007/0068995 A1 | 3/2007 | Kley | |
| 2007/0201866 A1 * | 8/2007 | Kihara | 396/468 |
| 2007/0276629 A1 * | 11/2007 | Koonankeil | 702/185 |
| 2009/0021018 A1 * | 1/2009 | Grichnik | 290/55 |
| 2009/0106805 A1 * | 4/2009 | Astigarraga et al. | 725/110 |
| 2009/0196597 A1 * | 8/2009 | Messinger et al. | 396/427 |
| 2009/0240280 A1 | 9/2009 | Wang et al. | |
| 2009/0247833 A1 * | 10/2009 | Tanaka | 600/188 |
| 2009/0309997 A1 * | 12/2009 | Hunt et al. | 348/240.2 |
| 2010/0011893 A1 * | 1/2010 | Kawamoto | 74/411 |
| 2010/0092079 A1 * | 4/2010 | Aller | 382/165 |
| 2010/0133942 A1 * | 6/2010 | Hall et al. | 310/181 |
| 2011/0031760 A1 * | 2/2011 | Lugg | 290/55 |
| 2011/0162388 A1 * | 7/2011 | Barve et al. | 62/3.1 |
| 2011/0167687 A1 * | 7/2011 | Winkler | 40/440 |

FOREIGN PATENT DOCUMENTS

| | | |
|---|---|---|
| DE | 19859952 | 2/2000 |
| DE | 20307024 | 8/2003 |
| DE | 10255348 | 11/2003 |
| DE | 202004006503 | 9/2004 |
| DE | 202006003427 | 9/2006 |
| EP | 335126 | 3/1989 |
| EP | 943916 | 9/1990 |
| EP | 432743 | 12/1990 |
| EP | 1251164 | 4/2002 |
| EP | 1747835 | 7/2005 |
| JP | 56114612 | 2/1980 |
| JP | 56135087 | 3/1980 |
| JP | 57160362 | 3/1981 |
| JP | 58146765 | 2/1982 |
| JP | 4203510 | 12/1987 |
| JP | 63132108 | 6/1988 |
| JP | 2084312 | 7/1988 |
| JP | 2130772 | 11/1988 |
| JP | 2179364 | 12/1988 |
| JP | 3113785 | 9/1989 |
| JP | 3172605 | 12/1989 |
| JP | 2163604 | 6/1990 |
| JP | 4041214 | 6/1990 |
| JP | 5026965 | 7/1991 |
| JP | 5083852 | 9/1991 |
| JP | 5084765 | 9/1991 |
| JP | 5169454 | 12/1991 |
| JP | 5192855 | 1/1992 |
| JP | 5277585 | 3/1992 |
| JP | 4294116 | 10/1992 |
| JP | 6165511 | 11/1992 |
| JP | 6226705 | 2/1993 |
| JP | 7156032 | 12/1993 |
| JP | 8303477 | 5/1995 |
| JP | 8326726 | 5/1995 |
| JP | 9047805 | 8/1995 |
| JP | 9089904 | 9/1995 |
| JP | 9310343 | 5/1996 |
| JP | 9145340 | 6/1997 |
| JP | 1228743 | 3/1998 |
| JP | 11320204 | 5/1998 |
| JP | 2000176763 | 12/1998 |
| JP | 2001162472 | 12/1999 |
| JP | 2002260711 | 2/2001 |
| JP | 2004140202 | 10/2002 |
| JP | 2004195855 | 12/2002 |
| JP | 2005285307 | 3/2004 |
| JP | 2005320749 | 5/2004 |
| JP | 2005326357 | 5/2004 |
| JP | 2007296987 | 5/2006 |
| JP | 2009139199 | 12/2007 |
| JP | 2008184871 | 1/2008 |
| WO | WO 9325991 | 12/1993 |
| WO | WO 9529427 | 11/1995 |
| WO | WO 2004044420 | 5/2004 |
| WO | WO 2007017692 | 2/2007 |
| WO | WO 2009076942 | 6/2009 |
| WO | WO 2009109288 | 9/2009 |

* cited by examiner

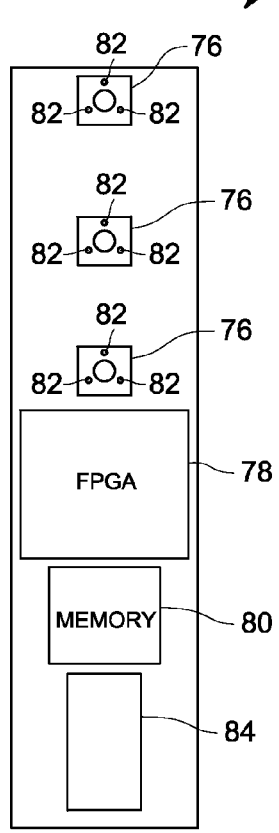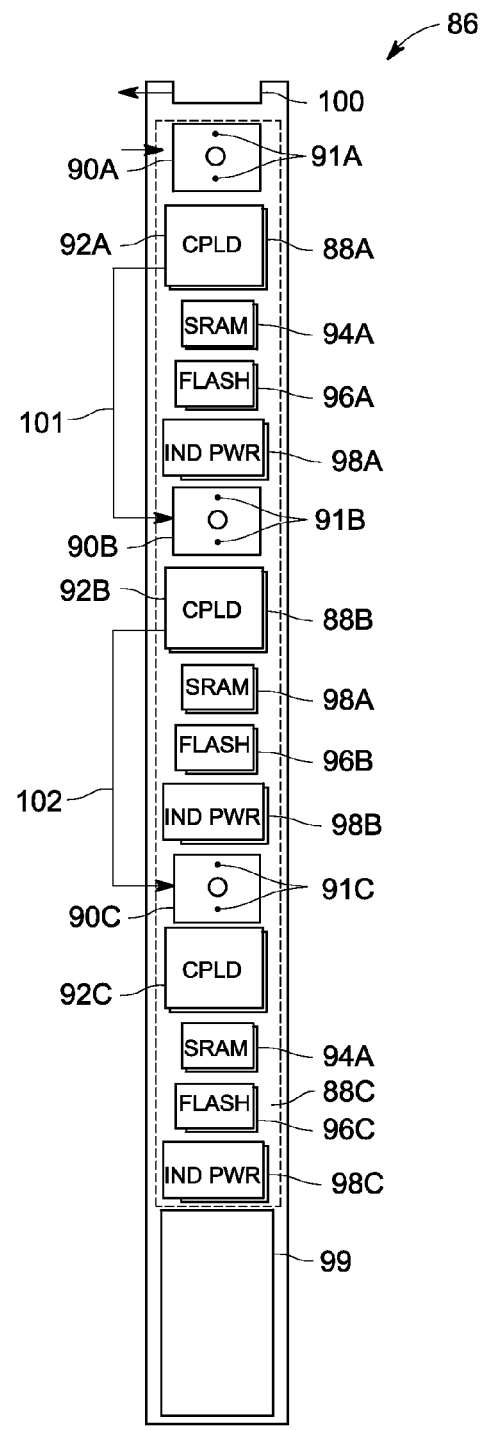
FIG. 6
FIG. 7

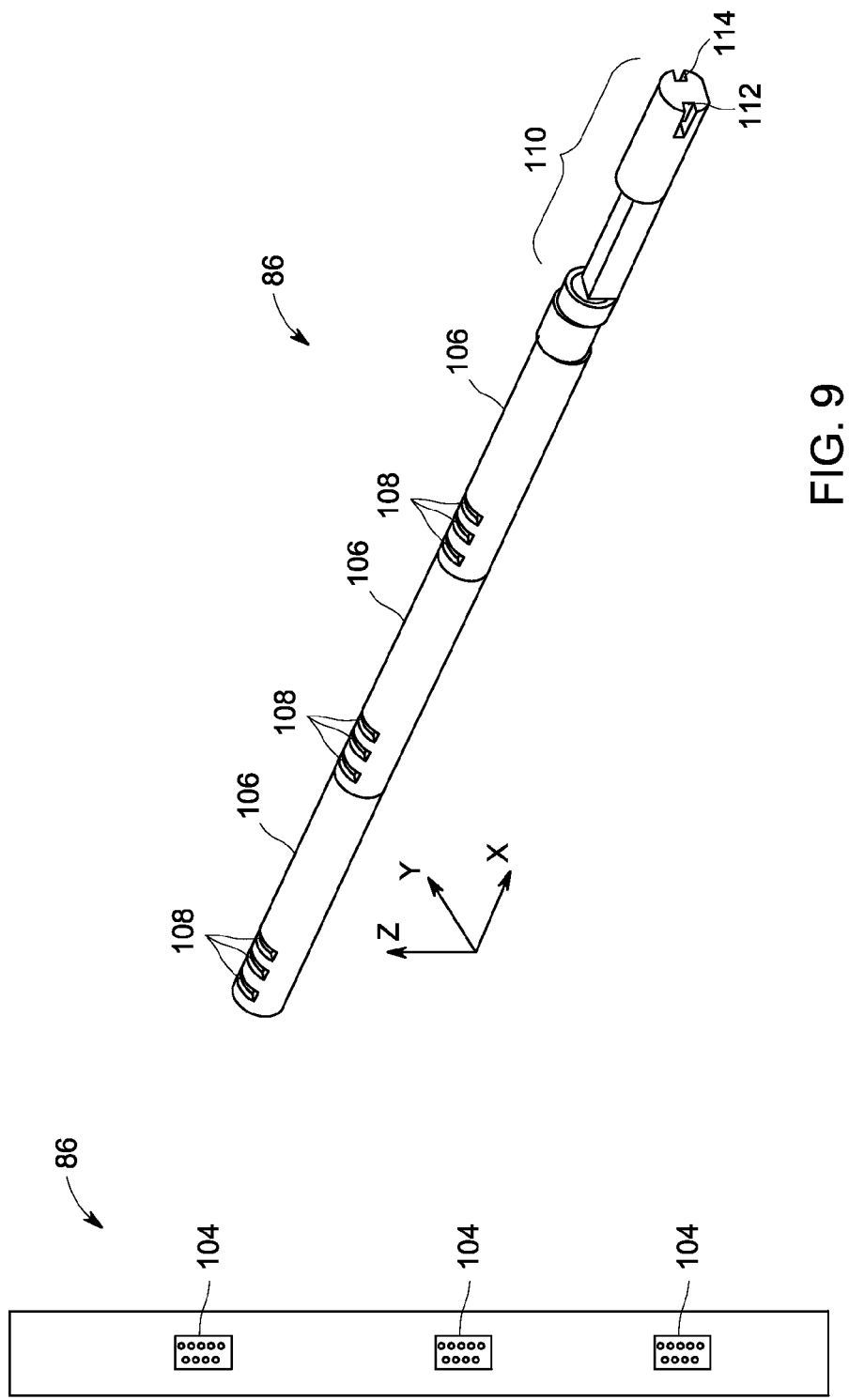

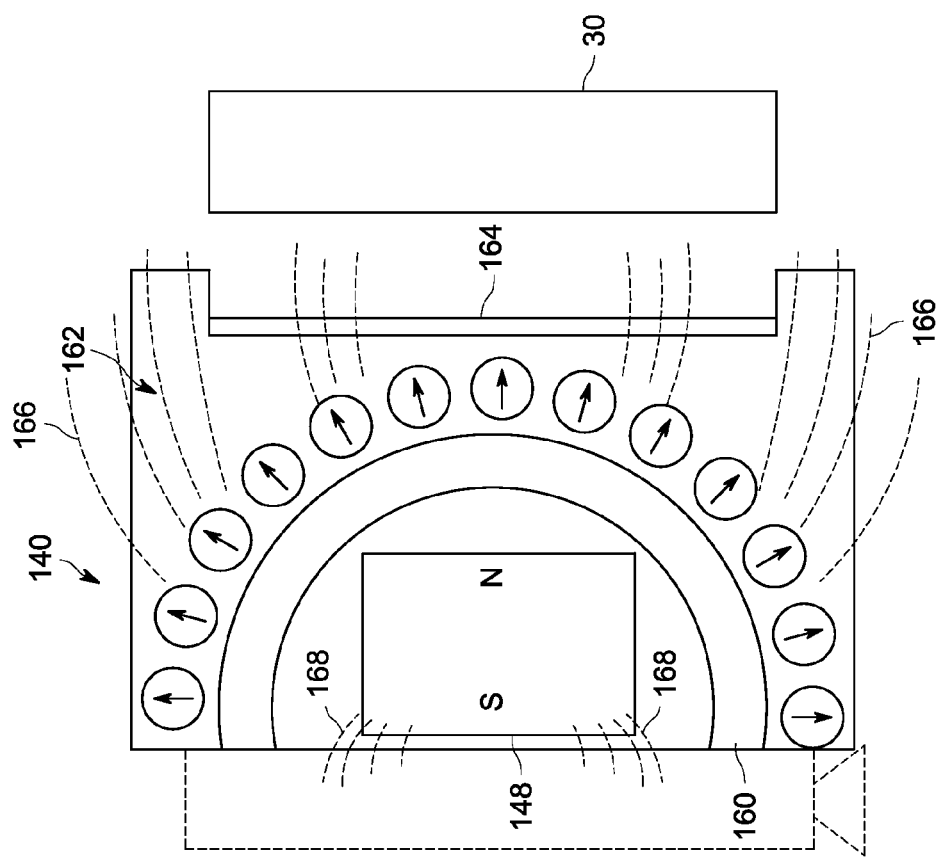

IMAGE RECORDING ASSEMBLIES AND COUPLING MECHANISMS FOR STATOR VANE INSPECTION

BACKGROUND OF THE INVENTION

The subject matter disclosed herein relates to gas turbine engines and, more particularly, to inspection of interior components of such turbine engines.

In general, gas turbine engines combust a mixture of compressed air and fuel to produce hot combustion gases. The combustion gases may flow through one or more turbine stages to generate power for a load and/or a compressor. The compressor may include rotary components, such as rotors and blades that rotate about a shaft, and stationary components, such as stator vanes. Over time, the various components of the compressor of the gas turbine engine may wear or develop defects. Inspection of these components to determine wear and/or defects may be difficult due to the enclosure of the gas turbine engine.

One technique for inspecting internal components of the gas turbine engine may include inserting a borescope through borescope holes to manually inspect different components, such as rotor blades or stator vanes. Unfortunately, such inspections using a borescope are time consuming and labor intensive. Additionally, the field of view of the borescope is limited and may not provide complete inspection coverage of all internal components of the gas turbine engine. Further, the borescope lens may have limitations in the depth of field and resolution, thus making interpretations and qualification of the borescope images difficult and ambiguous. Other inspection procedures may require removal of the compressor housing and disassembly of the compressor to inspect internal components.

BRIEF DESCRIPTION OF THE INVENTION

In one embodiment, a system for recording images of a stator vane of a compressor is provided that includes a first subassembly that includes a first image recording device coupled to a first printed circuit board (PCB), a non-volatile memory coupled to the first PCB, a volatile memory coupled to the PCB, and a first processor coupled to the PCB, wherein the first subassembly is coupled to a mechanism to form an image recording assembly, wherein the mechanism couples the image recording assembly to a blade of the compressor.

In another embodiment, a system is provided that includes an image recording assembly for recording images of a stator vane of a compressor and a mechanism configured to magnetically couple the image recording assembly to a blade of the compressor.

In another embodiment, a method is provided that includes inserting an image recording assembly into a compressor housing of a gas turbine engine, activating an image recording device of the image recording assembly, and activating a magnetic mechanism to couple the image recording assembly to a rotor blade of a compressor of the gas turbine engine

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 6 is a front schematic view of an image recording assembly in accordance with an embodiment of the present invention;

FIG. 7 is a front schematic view of an image recording assembly in accordance with another embodiment of the present invention;

FIG. 8 is a back schematic view of the image recording assembly of FIG. 7 in accordance with an embodiment of the present invention;

FIG. 9 is a front perspective view of the image recording assembly of FIG. 7 in accordance with an embodiment of the present invention;

FIG. 19 is a close-up top schematic view of the Halbach array coupling mechanism of FIG. 17 in accordance with another embodiment of the present invention;

DETAILED DESCRIPTION OF THE INVENTION

Embodiments of the present invention include an image recording assembly (e.g., a camera-based probe) for use in an inspection system to inspect internal components of a compressor of a gas turbine engine. The image recording assembly may include data processing and storage components, a light source, and a power source. Additional embodiments of the present invention include attachment mechanisms to secure the image recording assembly to a blade of a compressor. Such embodiments may include magnetic keepers, a Halbach array, and electro-permanent magnets.

The image recording assembly and attachment mechanisms described herein may be removably coupled to a rotary component of a compressor, e.g., a rotor blade, and used to record images of stationary components, e.g., stator vanes, of the compressor, without removal of the compressor housing or disassembly of the compressor. Such a technique is described in U.S. patent application Ser. No. 12/714,207, which is hereby incorporated by reference in its entirety for all purposes.

Figure 1:
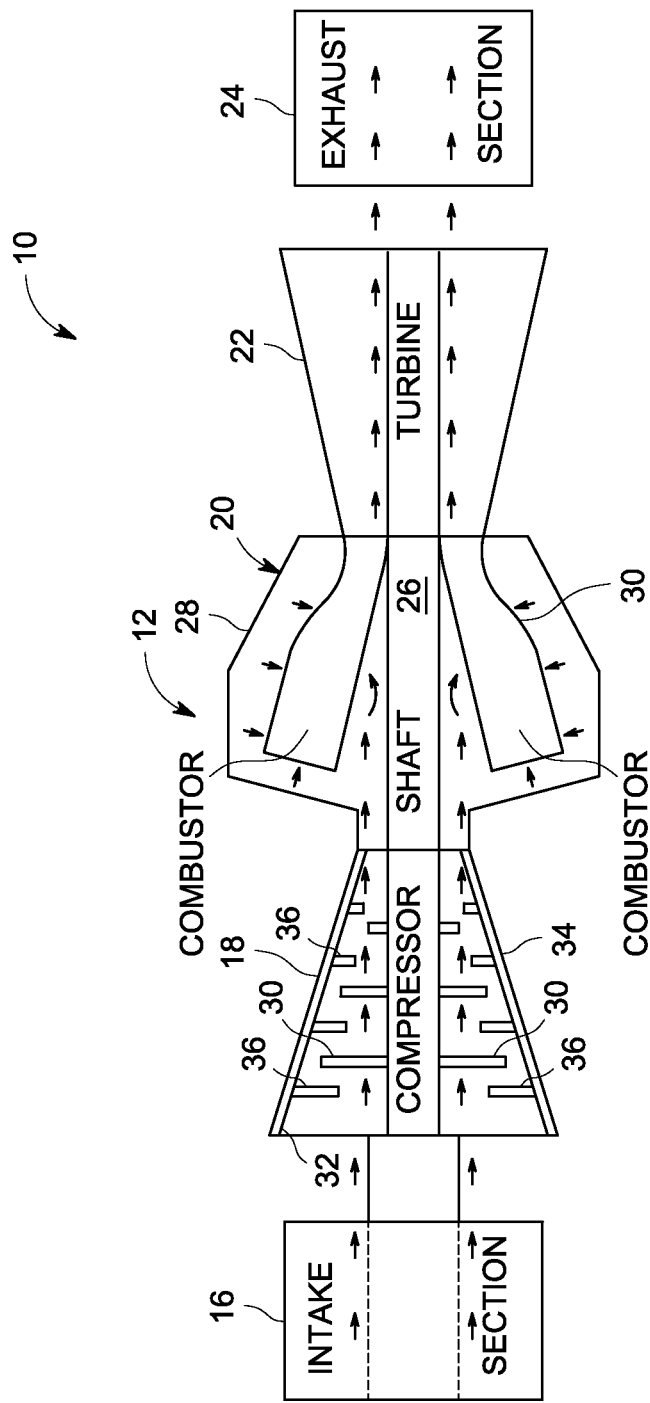
FIG. 1 is a schematic flow diagram of a gas turbine engine that may be inspected in accordance with an embodiment of the present invention.

With the foregoing in mind, FIG. 1 is a block diagram of an exemplary system 10 including a gas turbine engine 12 that may be inspected using the inspection system described herein. In certain embodiments, the system 10 may include an aircraft, a watercraft, a locomotive, a power generation system, or combinations thereof. The illustrated gas turbine engine 12 includes an air intake section 16, a compressor 18, a combustor section 20, a turbine 22, and an exhaust section 24. The turbine 22 is coupled to the compressor 18 via a shaft 26.

As indicated by the arrows, air may enter the gas turbine engine 12 through the intake section 16 and flow into the compressor 18, which compresses the air prior to entry into the combustor section 20. The illustrated combustor section 20 includes a combustor housing 28 disposed concentrically or annularly about the shaft 26 between the compressor 18 and the turbine 22. The compressed air from the compressor 18 enters combustors 29 where the compressed air may mix and combust with fuel within the combustors 29 to drive the turbine 22. The combustion of the air and fuel may generate hot pressurized exhaust gases, which may then be utilized to drive one or more turbine blades within the turbine.

The compressor 18 may include rotor blades 30 coupled to the shaft 26. The compressor blades 30 may span the radial gap between the shaft 24 and an inner wall or surface 32 of a compressor housing 34 in which the internal components of the compressor are disposed. As used herein, the term rotor blades 30 may also refer to "rotor buckets," e.g., the rotor blade and various components. The compressor 18 may include a rotor that couples each of the rotor blades 30 to the shaft 26. The compressor 18 may include stationary components, e.g., stator vanes 36, extending from the inner wall or surface 32 and axially offset from and adjacent to the rotor blades 30. The rotation of the shaft 26 causes rotation of the rotor blades 30, thereby drawing air into the compressor 18 and compressing the air prior to entry into the combustor section 20.

Figure 2:
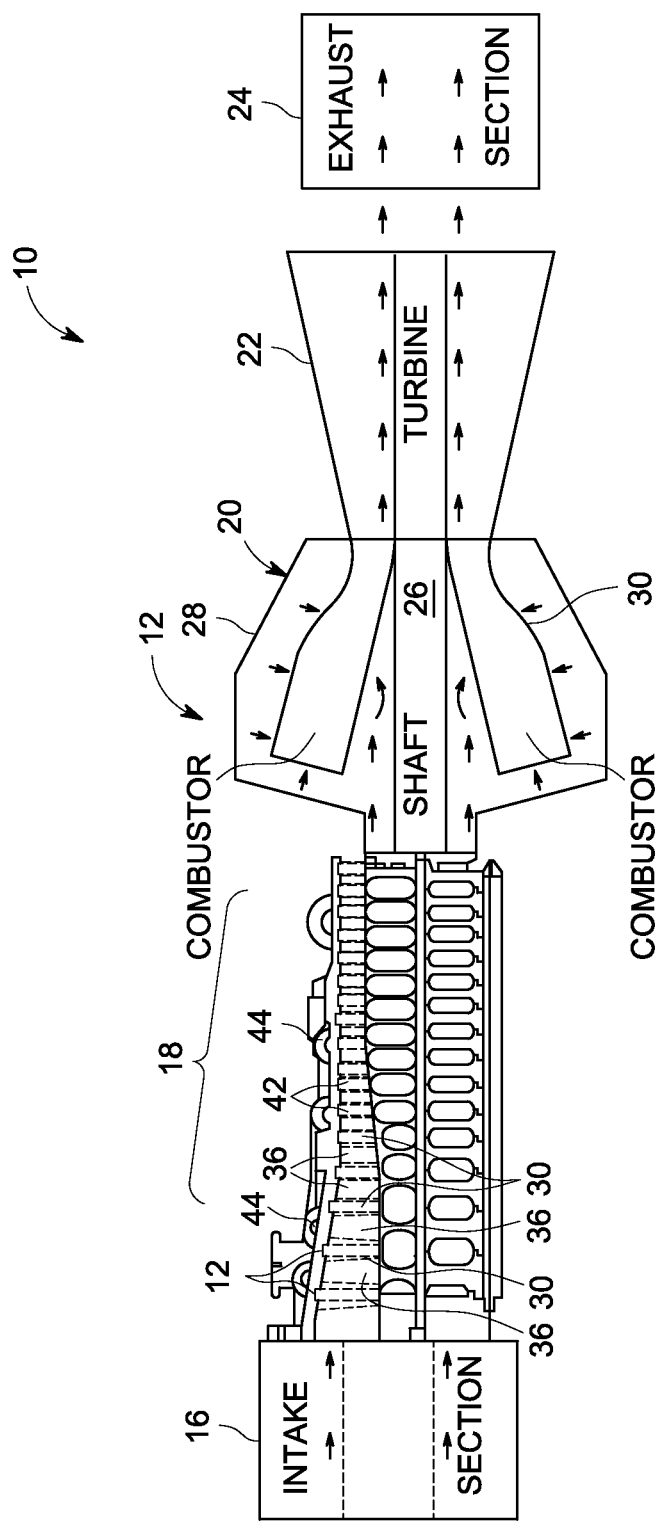
FIG. 2 is a sectional view of the compressor of the gas turbine engine of FIG. 1 sectioned through the longitudinal axis in accordance with an embodiment of the present invention.

FIG. 2 is a sectional view of the compressor 18 of the gas turbine engine 12 of FIG. 1 taken along the longitudinal axis 40. As depicted, the compressor 18 may include multiple rotary stages 42. Each stage may include rotary components, such as a rotor blades 30 coupled to a rotor that may be rotatably attached to the shaft 26 (FIG. 1). The blades 30 may extend radially outward from the rotor and may be partially disposed within the path of the gases and between concentric portions of stator vanes 36. The stator vanes 36 may be arranged in a circumference around the shaft 26.

As described above with respect to FIG. 1, air may enter through the air intake section 16 and be compressed by the compressor 18. The compressed air from the compressor 18 may then be directed into the combustor section 20 where the compressed air may be mixed with fuel gas. The mixture of compressed air and fuel gas is generally burned within the combustor section 20 to generate high-temperature, high-pressure combustion gases, which may be used to generate torque within the turbine 22.

During operation of the gas turbine engine 12, internal components of the compressor 18 may develop wear and/or defects. For example, the stator vanes 36 may gradually wear or develop defects that affect efficiency and output of the compressor 18. Such wear and defects may include, for example, cracks, corrosion, erosion, chipping, etc. In some embodiments, the gas turbine engine 12 may include borescope holes 44 disposed longitudinally along the compressor housing 34. The borescope holes 44 may provide for conventional inspection of interior components via a borescope. A borescope may be inserted into one of the borescope holes 44, through the housing 34 and the inner wall 32 of the compressor 18, to examine the stator vanes 36 and other internal components of the compressor 18. As described further below, the borescope holes 44 may provide access for an image recording assembly installed on the rotor blades 30 and used to record images of the stator vanes 36.

Figure 3:
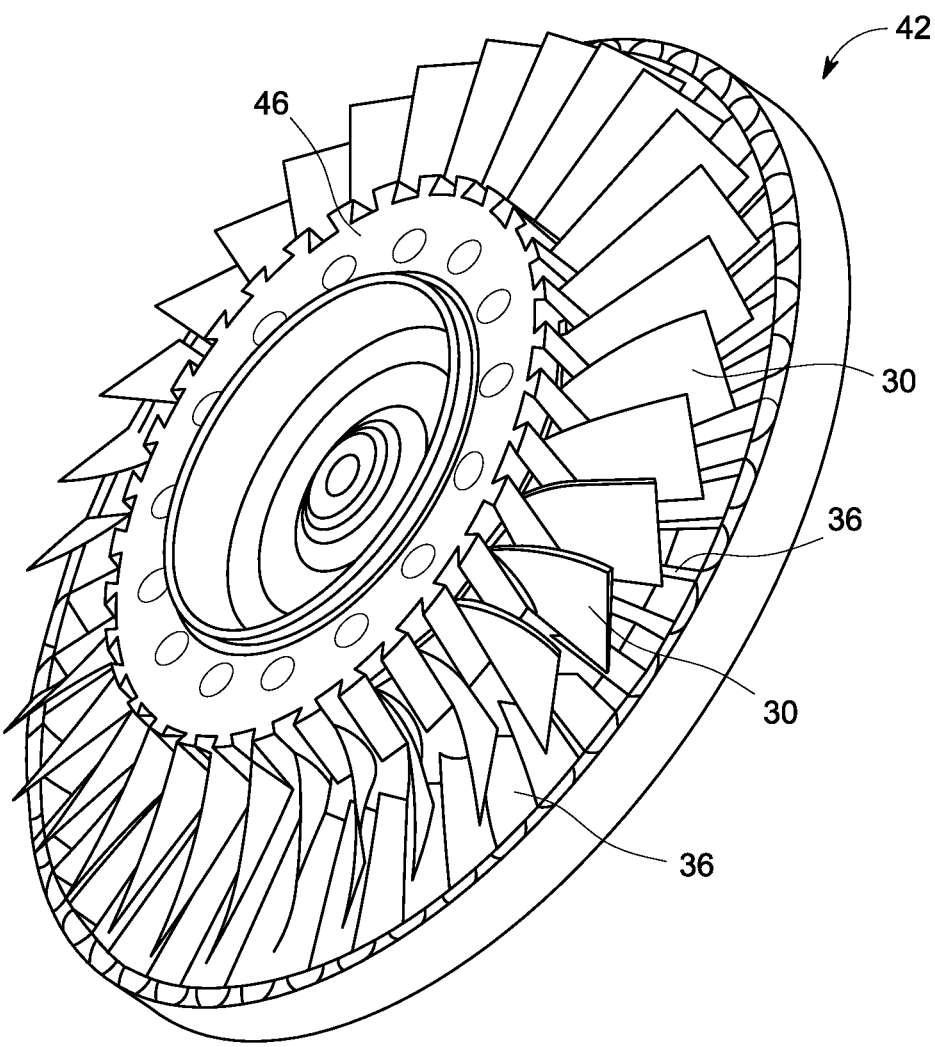
FIG. 3 is a perspective view of a stage of the compressor of the gas turbine engine of FIG. 1 in accordance with an embodiment of the present invention.

FIG. 3 is a perspective view of a stage 42 of the compressor 18. FIG. 3 further illustrates the stage 42 having a rotor 46 with rotor blades 30 extending radially therefrom. The stage 42 also shows the stator vanes 36 axially offset from and adjacent to the rotor blades 30 and extending radially toward the axis of rotation of the rotor 46. As seen in FIG. 3, the stator vanes 36 extend circumferentially around the axis of rotation of the rotor 46. As described below, embodiments of the present invention include image recording assemblies that may be secured to one or more rotor blades 30 of the compressor 18. The image recording assembly is secured to a rotor blade 30 and oriented to record images of the stator vanes 36. Additionally, image recording assemblies may be removably coupled to rotor blades on the other side of the stator vanes 36 to provide further coverage of the stator vanes 36. In other embodiments, image recording assemblies may be coupled to the space between rotor blades. As the rotor 46 rotates, the image recording assemblies also rotate around the axis of rotation, enabling the image recording device to record images of substantially all of the stator vanes 36 of the stage 42.

Figure 4:
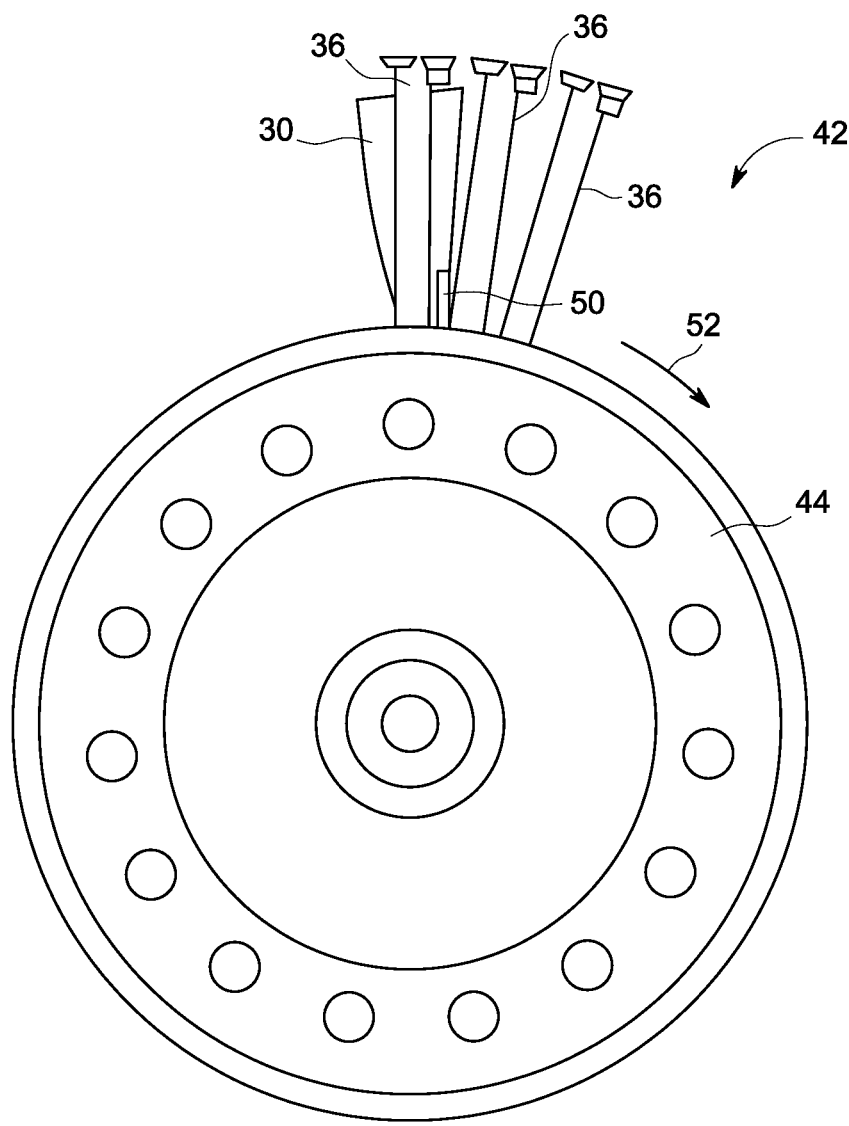
FIG. 4 is a front view of the stage of FIG. 3 with an image recording assembly in accordance with an embodiment of the present invention.

FIG. 4 depicts a front view of a stage 42 of the compressor 18 in accordance with an embodiment of the present invention. For clarity, only one rotor blade 30 and three stator vanes 36 are illustrated in FIG. 4. As shown in FIG. 4, an image recording assembly 50 is secured to the rotor blade 30. As described further below, the image recording assembly 50 may include an image recording device, a light source, a storage device, a power supply, and a coupling mechanism. The image recording assembly 50 may be secured to any portion of the rotor blade 30, and multiple assemblies 50 may be removably coupled along the radial length of the rotor blade 30. For example, as shown in FIG. 4, the image recording assembly 50 may be secured to the rotor blade 30 near the rotor 46. Thus, as the rotor 46 rotates (such as in the direction illustrated by arrow 52), the image recording assembly 50 rotates along the circumference of stator vanes 36. As the image recording assembly 50 rotates, the image recording assembly 50 may record images of the stator vanes 36 in the field of view of the image recording device. Thus, as the image recording assembly 50 rotates 360 degrees around the axis of rotation of the rotor 46, images of all of the circumference of stator vanes 36 may be recorded.

Figure 5:
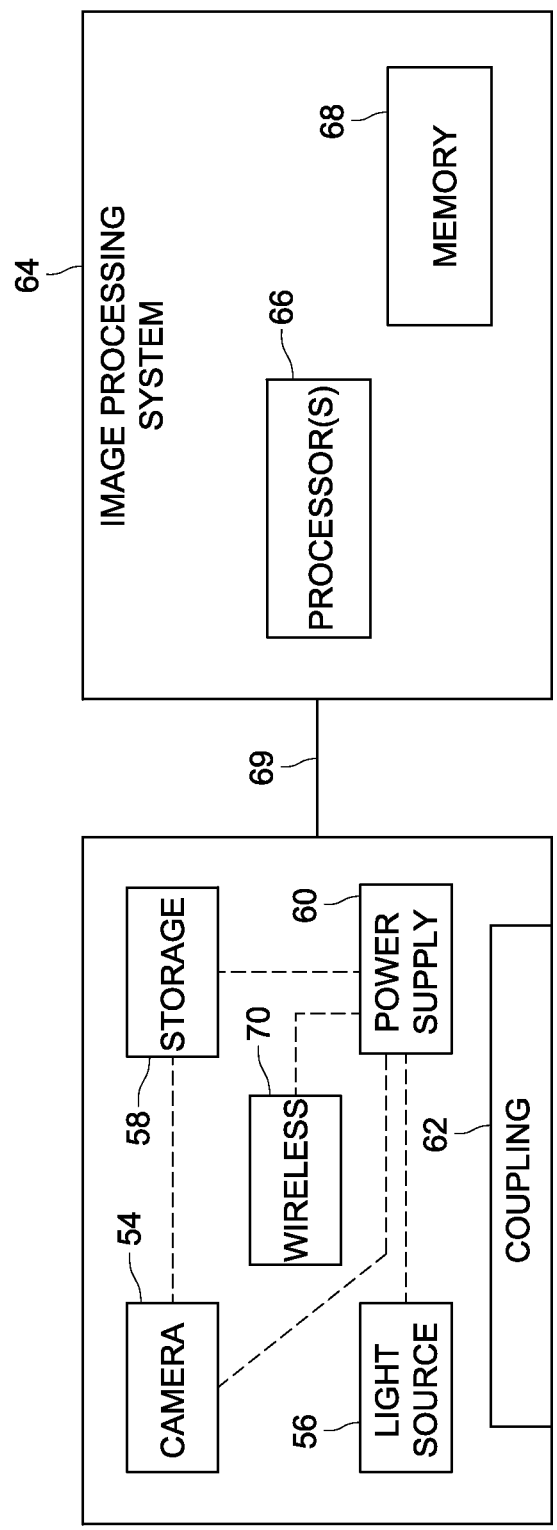
FIG. 5 is a block diagram of an image recording assembly and an imaging processing system in accordance with an embodiment of the present invention.

FIG. 5 depicts a block diagram of the image recording assembly 50 in accordance with an embodiment of the present invention. The image recording assembly 50 may include one or more image recording devices, e.g., cameras 54, one or more light sources 56, one or more storage devices 58 (e.g., non-volatile memory), one or more power supplies 60, and a coupling mechanism 62. Additionally, FIG. 5 depicts an image processing system 64 (e.g., a computer) having one or more processors 66 and memory 68 (e.g., volatile or non-volatile memory). When removed from the compressor 18, the image recording assembly 54 may be coupled to the image processing system 66 via a cable 69.

The image recording assembly 50 may include one camera oriented towards the stator vanes, or may include multiple cameras oriented in different directions. For example, the cameras 54 may be oriented to inspect the stator vanes of multiple stages on either side or the rotor wheel 32. The number of cameras used to obtain substantially 100% image coverage of a stator vane may be determined from the height of the stator vane and the field of view of the camera. For example, for a stator vane of 27 cm and a field of view diameter of 110 mm, the number of cameras used to provide substantially 100% coverage of the stator vane is approximately 3 (270/110).

The cameras 54 may include an analog camera and/or a digital camera and may receive power from the power supplies 60. In some embodiments, the cameras 54 may record images at a rate of at least about 2 frames-per-second (FPS) and may have a resolution of greater than at least 0.1 MP, 1 MP, 2 MP, or 3 MP. The cameras 54 may include a time mechanism to enable the camera to record images periodically after a specified time interval. Additionally, or alternatively, the cameras 54 may include a trigger mechanism that may be activated by rotation of the rotor blade 30.

In some embodiments, the image recording assembly 50 may include a video recording device, so that the image recording assembly 50 records video of the internal components of the compressor 18. In other embodiments, the image recording assembly 50 may include any other image sensing devices, such as infrared, ultrasound, and/or eddy current sensing devices.

The light source 56 may include light emitting diodes (LEDs), fluorescent lights, incandescent lights, or any other suitable light device, and may be oriented to illuminate the stator vanes 36 or any other region capable of image record by the cameras 54. Multiple color light sources may be used, such as blue, green, red, white, or other colors. For example, blue LEDs may be used during a first portion of the inspection and green LEDS may be used during a second portion of the inspection. The storage device 58 may be a non-volatile memory device (e.g., a flash memory device) configured to provide a desired storage capacity and maintain the small size of image recording assembly 50. In one embodiment, the storage device may provide at least 2 GB, 4 GB, 6 GB, or 8 GB of memory.

In some embodiments, a camera 54, a light source 56, and/or a storage device 56 may form an integrated assembly. In other embodiments a camera 54, a light source 56, and/or a storage device 58 may be individually selected and separately provided in the image recording assembly 50.

The one or more power supplies 60 may include one or more batteries, such as lithium ion, polymer lithium, nickel cadmium, or any other suitable batteries. In one embodiment, the power supplies 60 may include a battery having a capacity of at least about 250 mAh and a voltage of at least about 3 V. The power supplies 60 may be configured to provide for operation for the camera 54, the light source 56, and the storage device 58 for at least the duration of the inspection process.

The coupling mechanism 62 may be configured to provide enough force to secure the image recording assembly 50 against the centrifugal force produced by the rotating blade 30. For example, for an image recording assembly 50 having a weight of about 50 g, an image recording assembly placement of a radial distance of 500 mm from base of the rotor blade 30, and a rotor speed of 1 rpm, the centrifugal force is approximately 0.0003 N. The coupling mechanism 62 may include a magnetic coupling, a clamping mechanism, an adhesive, a pneumatic mechanism, or any other suitable mechanism or combination thereof.

As described further below in FIGS. 11-31, in some embodiments the coupling mechanism 62 may include a magnetic coupling mechanism, such as magnetic keepers, a Halbach array, electro-permanent magnets and/or moveable magnets. Additionally, the coupling mechanism 62 may include adhesive on a housing of the image recording assembly 50. As described below, the magnetic field produced by the magnets may be manipulated such that the coupling mechanism has an ON position (the magnetic field is directed outward from the coupling mechanism 62 so the camera assembly 50 can be coupled to a rotor blade) and an Off position (the magnetic field is concealed inside the coupling mechanism 62 so the camera assembly 50 can be detached from a rotor blade). In yet other embodiments, the coupling system 62 may include a pneumatic system may include an array of micro suction cups and a micro air pump to create a vacuum force and allow the suction cups to couple the image recording assembly 50 to a rotor blade. In some embodiments, as described further below, actuation of any of the coupling mechanisms 62 described above may be through a switch included in the image recording assembly 50 and operable by a tool used to insert the image recording assembly 50.

In some embodiments, the image recording assembly 50 may include a wireless communication device 70 that may be used to transmit images from the cameras 54 and/or storage devices 58 to the image processing system 64. Alternatively, in other embodiments the image recording assembly 50 may be physically connected to the image processing system 64 via the cable 69, when the image recording assembly 50 is removed from the gas turbine engine 12. For example, the image recording assembly 50 may be coupled to the image processing system 64 via a Universal Serial Bus (USB) interface, Firewire interface, eSata interface, or any other suitable interface. The image processing system 64 may also be capable of processing any data received from the image recording assembly 50, such as still images, video, infrared images, ultrasound images, eddy current images, etc.

FIG. 6 depicts a front schematic view of an embodiment of an image recording assembly 74 having three cameras 76 arranged longitudinally on the assembly 74. In some embodiments, the cameras 76 may include an OV9665FF camera and/or an O2665AF camera manufactured by Supertech Optoelectronics of Taipei, Taiwan. The image recording assembly 74 may include an FPGA 78, a storage device 80, LEDs 82, and a power source 84 (e.g., a battery). Each camera 76 may be surrounded by three LEDs 82. The FPGA 78 may control and synchronize the subsystems of the assembly 74. In the embodiment depicted in FIG. 6, the components may be provided and assembled on a single PCB. The image recording assembly 74 depicted in FIG. 6 may have a width of approximately 19 mm and a length of about 120 mm In this embodiment, the cameras 76 may have a length of 12 mm and a width of 12 mm The image recording assembly 74 may be capable of recording and processing 8-bit images at least 30 frames-per-second (fps), and may record color images.

FIG. 7 depicts a front schematic view of an image recording assembly 86 in accordance with another embodiment of the present invention. The recording assembly 86 may include subassemblies 88A, 88B, and 88C. The components of each subassembly 88 may each be assembled on an individual PCB, or all the subassemblies may be assembled on a single PCB. Each subassembly 88 may include a camera 90, light sources 91, a complex programmable logic device (CPLD) 92, volatile storage 94 (e.g., SRAM), non-volatile storage 96 (e.g., flash memory) and power circuitry 98. The image recording assembly 86 may also include a power source 99 (e.g., a battery). Additionally, the image recording assembly 86 may include a switch 100 coupled to the camera 90A of the first subassembly 88A. In some embodiments, the cameras 90 may include an OV7690 camera manufactured by Supertech Optoelectronics of Taipei, Taiwan. Further, the cameras 90 may have a length of 4 mm and a width of 5 mm The image recording assembly 86 may be capable of recording and processing 8-bit images at least 10 frames-per-second (fps). The power circuitry 98 may include a power booster integrated circuit, a power regulator, a surface mount inductor (SMD), or any other suitable circuits or components.

In some embodiments, the switch 100 may be a collapsible switch configured to provide a signal for the cameras 90 or other components of the assembly 86 and operate a motor for actuating a coupling mechanism, as described below. For example, the collapsible switch may be collapsed to turn the image recording assembly 86 "OFF" and may be released to turn the image recording assembly 86 "ON." The collapsible switch may include a spring to bias the switch to the released position. In other embodiments, the switch 100 may be a push button or other type of switch.

The switch 100 may be used to activate the camera 90A of the first subassembly 88A. The switch 100 may send a signal directly to the camera 90A or to the CPLD 92A, which may then activate the camera 90A to start recording images. To synchronize the operation of the three cameras 90A, 90B, and 90C, a START signal, illustrated by arrow 101, may be provided from the CPLD 92A to the second camera 90B on the second subassembly 88B. Similarly, a START signal, illustrated by arrow 101, may be provided from the CPLD 92B to the third camera 90C. In this manner, the activation of the switch 100 may cause activation of the cameras 90A, 90B, and 90C.

During insertion of the image recording assembly 86, the collapsible switch may be collapsed via a tool (e.g., alligator clips) and then released when the image recording assembly 86 is in position. Such a tool may also include a flexible cable, an image sensor, and an electromagnet, to enable easier viewing and manipulation of the image recording assembly 86 when it is inserted into the compressor 18. The coupling mechanism may secure the image recording assembly 86 after release of the alligator clips to ensure secure coupling to the rotor blade. In one embodiment, the tool may include borescope tools available from GE Inspection Technologies of Lewistown, Pa.

FIG. 8 depicts a back schematic view of the image recording assembly 86 in accordance with an embodiment of the present invention. As shown in FIG. 8, the image recording assembly 86 may include one or more connectors 104 to connect the image recording assembly to the image processing system 64. The connectors 104 may be any suitable connector and interface, such as USB, Firewire, serial port, etc.

Figure 10:
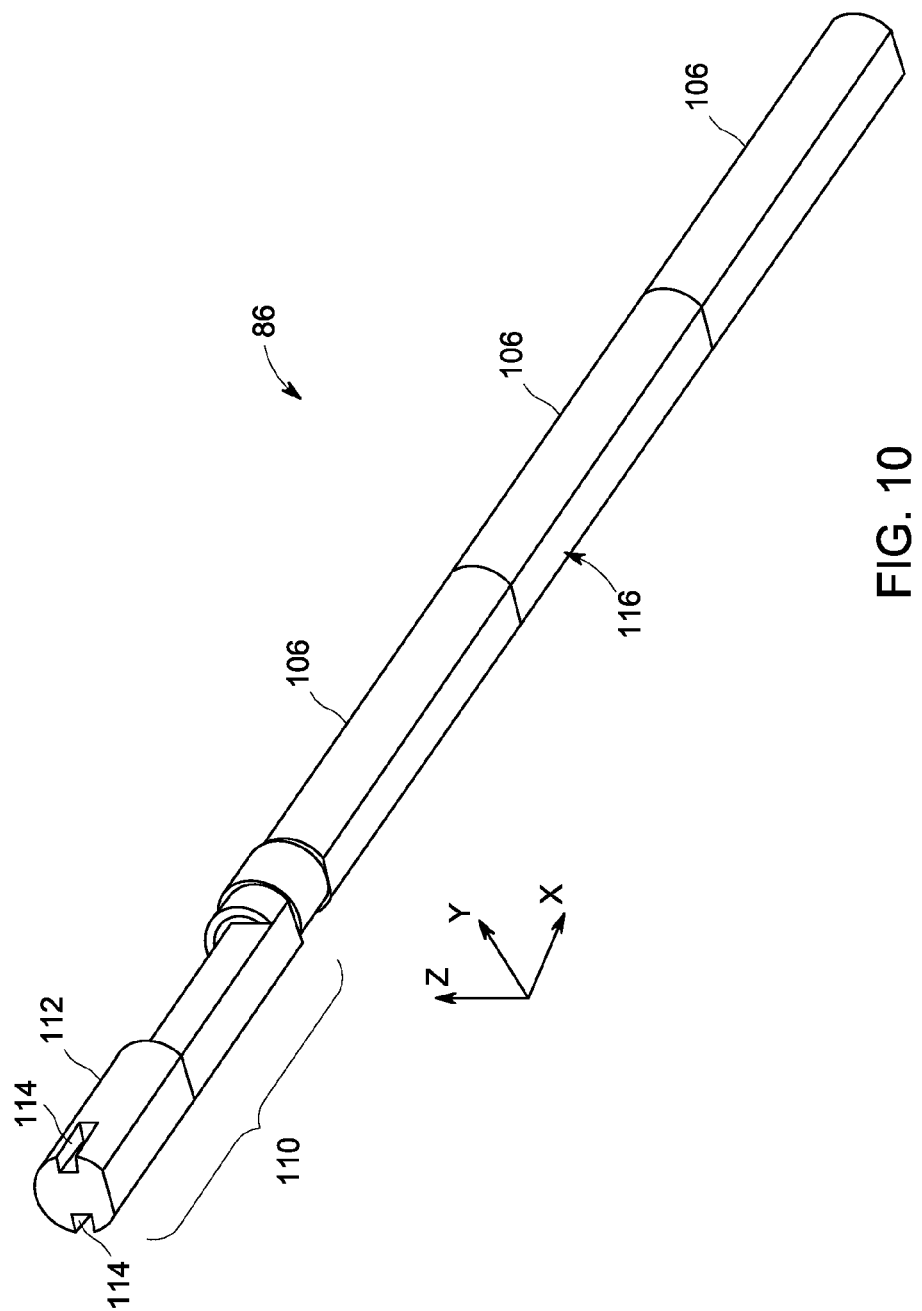
FIG. 10 is a rear perspective view of the image recording assembly of FIG. 7 in accordance with an embodiment of the present invention.

FIGS. 9 and 10 are front and rear perspective views respectively of the image recording assembly 86 in accordance with an embodiment of the present invention. As shown in FIGS. 9 and 10, the image recording assembly 86 may be enclosed in a housing 106. Each portion of the housing 106 covering each subassembly 88 may include holes 108 to expose the light sources 91 and cameras 90. The housing 106 may be a single housing or may be individual housings that each cover one of the subassemblies 88. The image recording assembly 86 may also include an end portion 110 having a handle 112. The handle 112 may include notches 114 or other suitable features to receive a "gripper" or other tool for inserting the image recording assembly 86 into the compressor 18. Additionally, the handle 112 may be gripped, released, rotated, translated, or otherwise manipulated to activate the switch 100.

As shown in FIG. 10, one side of the housing 106 may include a relatively flat portion 116 to ensure that the image recording assembly 86 can be coupled to the blade of the compressor 18. The flat portion 116 may provide a surface area for a coupling mechanism to provide coupling forces to the area of the blade with which the image recording assembly 86 and flat portion 116 are aligned.

As mentioned above, the coupling mechanisms for the above embodiments may include magnetic coupling mechanisms. Such mechanisms may include, for example, magnetic keepers, as described below in FIGS. 11-16, a Halbach array, as described below in FIGS. 17-19, electro-permanent magnets, as described below in FIGS. 20-23, and movable magnets, as described below in FIGS. 24-31.

Figure 12:
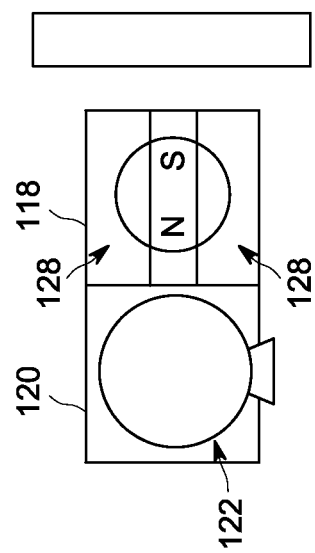
FIG. 12 is a top schematic view of the magnetic keepers coupling mechanism of FIG. 11 in accordance with an embodiment of the present invention.
Figure 11:
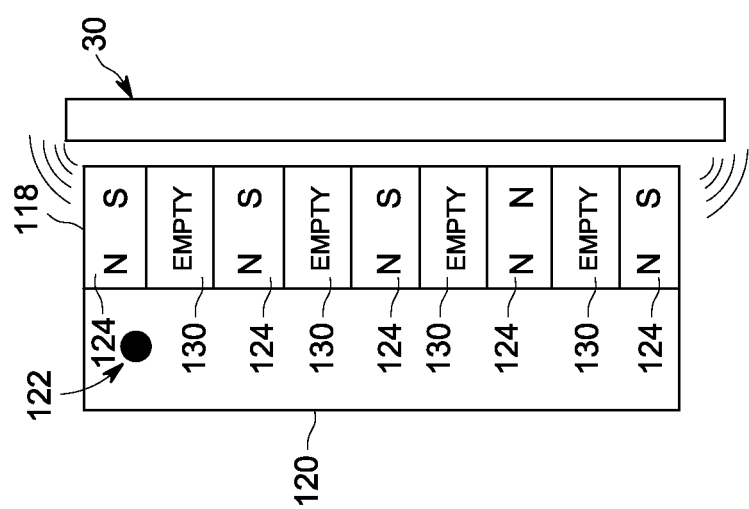
FIG. 11 is a front schematic view of a magnetic keepers coupling mechanism of an image recording assembly in accordance with an embodiment of the present invention.

FIG. 11 is a schematic front view of a magnetic keepers coupling mechanism 118 of an image recording assembly 120, and FIG. 12 is a schematic top view of the magnetic keepers coupling mechanism 118 and the image recording assembly 120 in accordance with an embodiment of the present invention. The schematic of FIG. 11 may depict a portion of or the entire image recording assembly 120 that may include one or more image recording devices 122. The magnetic keepers coupling mechanism 118 may couple the image recording assembly 120 to the blade 30 of a compressor.

As shown in FIG. 11, the magnetic keepers coupling mechanism 118 may include a plurality of magnets 124 to produce a magnetic field. The magnetic keepers coupling mechanism 118 may include keepers 128 arranged across the poles of the magnets 124. The magnets 124 may be arranged along the length of the image recording assembly 120 and may include spacers 130. The magnetic field produced by the coupling mechanism 118 couples the image recording assembly 120 to the blade 30.

Figure 13:
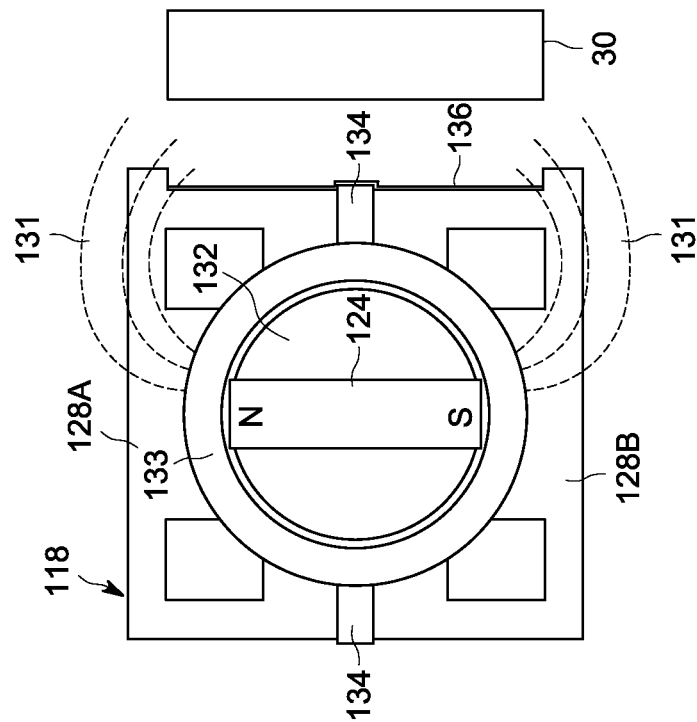

FIG. 13 is a close-up top schematic view of the magnetic keepers coupling mechanism 118 in accordance with an embodiment of the present invention. FIG. 13 depicts the magnetic keepers coupling mechanism 118 in the "ON" position such that a magnetic field 131 is generated by the magnets 124 to couple the mechanism 118 to the blade 30. The magnets 124 may be retained by a magnet holder 132 which may be a polymer or other suitable material. The magnets 124 and magnet holder 132 may be surrounded and, in some embodiments, retained by, a non-magnetic tube 133. The magnetic keepers 128 may include a first keeper 128A and a second keeper 128B. The keepers 128A and 128B may be separated by a non-magnetic strip 134. The magnetic keepers coupling mechanism 118 may also include a coating 136 (e.g., Teflon) on the surface of the mechanism 118 that couples to the blade 30.

Figure 14:
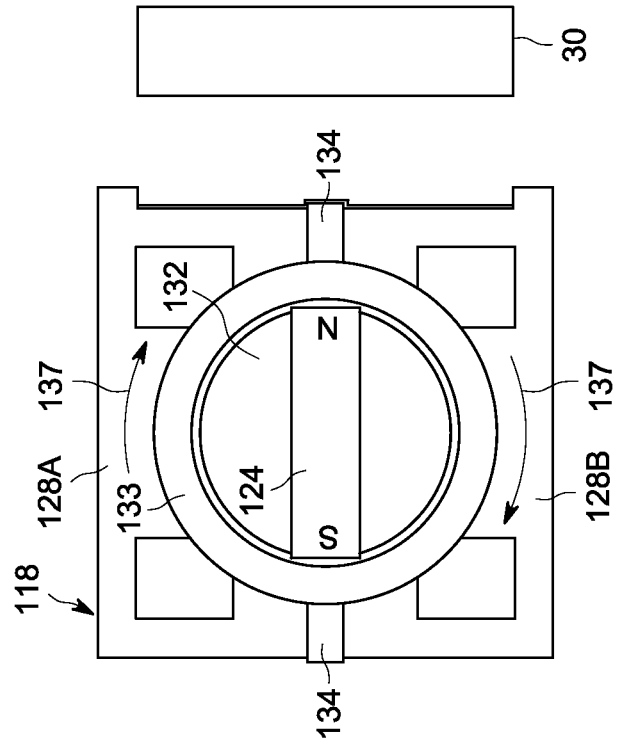
FIGS. 13 and 14 are a close-up top schematic views of the magnetic keepers coupling mechanism of FIG. 11 in accordance with an embodiment of the present invention.

FIG. 14 is a close-up top schematic view of the magnetic keepers coupling mechanism 118 illustrating the mechanism 118 in an "OFF" position in accordance with an embodiment of the present invention. As shown in FIG. 14, in the "OFF" position the magnets 124 may be rotated, such in the direction indicated by arrow 137, such that the magnets 124 are parallel to the non-magnetic strip 134. In this position, the non-magnetic strip 134 prevents external production of the magnetic field 131 and the coupling mechanism 118 may be freely removed from the blade 30, allowing removal of the image recording assembly 120 from the compressor 18.

Figure 16:
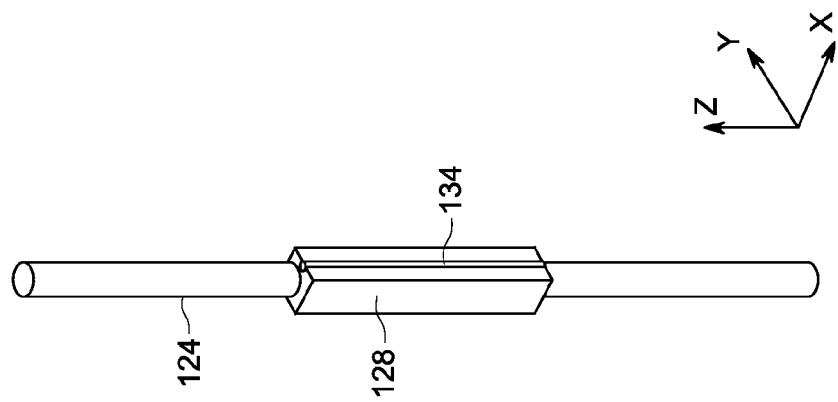
FIGS. 15 and 16 are side perspective views of the magnetic keepers coupling mechanism of FIG. 11 in accordance with an embodiment of the present invention.
Figure 15:
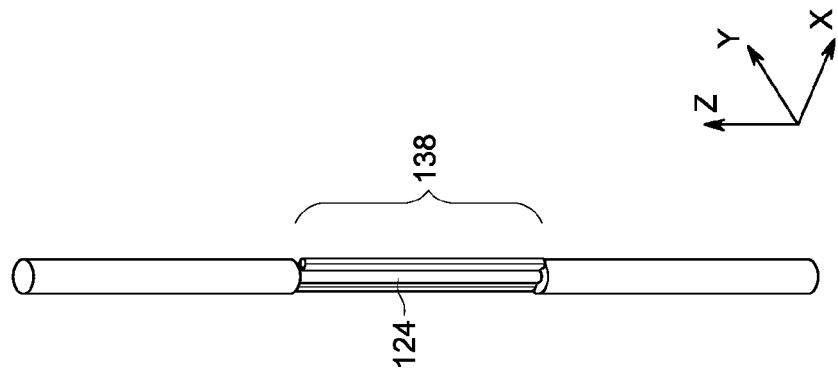

FIG. 15 depicts a side perspective view of the magnetic keepers coupling mechanism 118 in accordance with an embodiment of the present invention. FIG. 15 depicts the non-magnetic tube 124, the magnetic keeper 128, and the non-magnetic strip 134. The magnetic tube 124 may be copper or other suitable non-magnetic material, such as a non-ferrous metal or alloy, and the non-magnetic strip 134 may be brass or other suitable non-magnetic material, such as a non-ferrous metal or alloy. The magnetic keeper 128 may be iron or any suitable ferrous alloy, such as mild steel or low carbon steel. The magnetic keeper 128 and the non-magnetic strip 134 may be disposed along the entire length of the non-magnetic tube 124, along a single portion of the non-magnetic tube 124, or at multiple intermittent portions along the non-magnetic tube 124. Thus FIG. 15 may only depict a portion of the magnetic keeper 128 and non-magnetic strip FIG. 16 depicts a side perspective view of the magnetic keepers coupling mechanism 118 with a section 138 of the non-magnetic tube 126 removed. As shown in FIG. 16, a portion of the magnets 124 are illustrated. As mentioned above, some embodiments may include a magnet holder 132 (not shown) disposed around the magnets 124. The magnets 124 may extend along the entire length of the non-magnetic tube 124, along a single portion of the non-magnetic tube 124, or at multiple intermittent portions along the non-magnetic tube 124. Additionally, as noted above, the magnets may be rotated around the z-axis to turn the magnetic keepers coupling mechanism 118 "ON" or "OFF."

Figure 17:
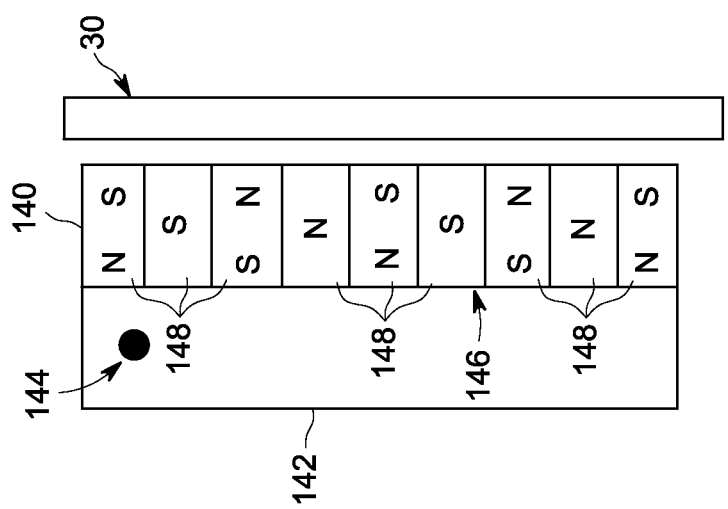
FIG. 17 is a front schematic view of a Halbach array coupling mechanism of an image recording assembly in accordance with an embodiment of the present invention.

As mentioned above, other embodiments may include a Halbach array coupling mechanism. FIG. 17 depicts a schematic side view of a Halbach array coupling mechanism 140 of an image recording assembly 142 in accordance with an embodiment of the present invention. The schematic of FIG. 17 may depict a portion of or the entire image recording assembly 142 that includes one or more image recording devices 144. The Halbach array coupling mechanism 140 may couple the image recording assembly 142 to the blade 30 of the compressor 18.

As shown in FIG. 17, the Halbach array coupling mechanism 140 may include a plurality of magnets 148 disposed along the length of the image recording assembly 142 and oriented to form a Halbach array. The magnets 148 may be separated from the image recording assembly by a keeper 146. FIG. 17 depicts an example of such an arrangement, wherein each of the plurality of magnets 148 has a different orientation than the adjacent magnets. As will be appreciated, the Halbach array arrangement produces a magnetic field on one side of the array and cancels the magnetic field on the opposite side of the array. Thus, the Halbach array coupling mechanism 140 couples the image recording assembly 144 to the blade 30 without producing a magnetic field in the opposite (non-blade side) direction.

Figure 18:
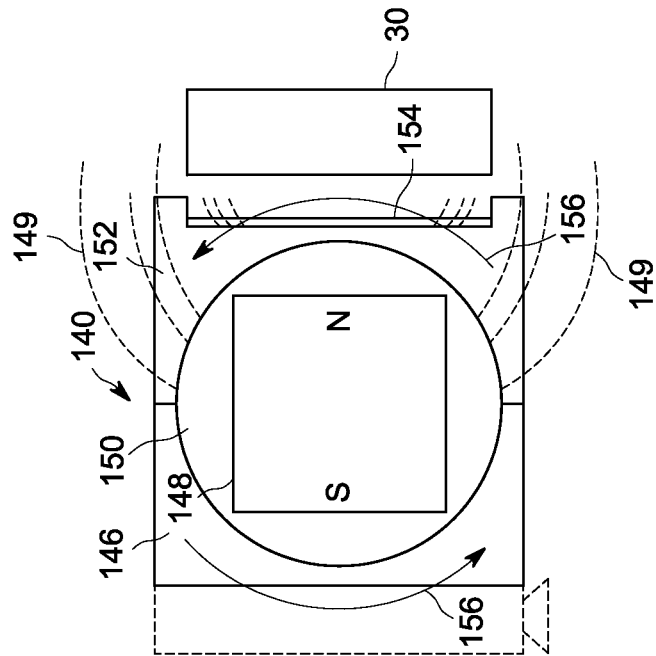
FIG. 18 is a close-up top schematic view of the Halbach array coupling mechanism of FIG. 17 in accordance with an embodiment of the present invention.

FIG. 18 is a top schematic view of an embodiment of the Halbach array coupling mechanism 140 in accordance with an embodiment of the present invention. As shown in FIG. 18, the Halbach array coupling mechanism 140 is depicted in an "ON" position, such that the magnets 148 are oriented to induce a magnetic field 149 towards the blade 30. The magnets 148 may be retained by a magnet holder 150 which may be a polymer or other suitable material. On the "blade" side of the Halbach array coupling mechanism 140, the magnets 148 may be surrounded and, in some embodiments, retained by, a non-magnetic block 152. The opposite side of the Halbach array coupling mechanism 140 may include the keeper 146 which may be iron or other ferrous alloy, such as mild steel or low carbon steel. The magnetic keepers coupling mechanism 140 may also include a coating 154, such as Teflon, on the surface of the mechanism 140 that couples to the blade 30.

As will be appreciated, the Halbach array coupling mechanism 140 may turned "OFF" by rotating the magnets 148 180-degrees, as indicated by arrows 156 in FIG. 18. Rotating the magnets 148 in this manner may change the orientation of the Halbach array so that the magnetic field 149 is no longer externally produced on the blade side of the Halbach array coupling mechanism 140. Additionally, it should be appreciated that magnets having a different shape (e.g. a differently shaped cross-section), may be used in the Halbach array described above. For example, although the magnets 148 depicted in FIG. 18 have a generally square cross-section, in other embodiments, magnets having circular cross-sections or rectangular cross-sections may also be used.

FIG. 19 depicts a top schematic view of another embodiment of the Halbach array coupling mechanism 140. In contrast to the embodiment depicted in FIG. 18, the magnets 148 of FIG. 19 may be enclosed by a semi-tubular magnetic keeper 160 which may be iron or any suitable ferrous alloy, such as mild steel or low carbon steel. A non-magnetic block 162 may be disposed over the magnetic keeper 160. As noted above, a coating 164, e.g., a Teflon coating, may be provided on the blade side of the Halbach array coupling mechanism 140. In such an arrangement, a magnetic field 166 from the Halbach array of magnets 148 may be produced toward the blade side of the Halbach array coupling mechanism 140. A less intense magnetic field 168 may be produced on the opposite side of the Halbach array coupling mechanism 140. The magnetic field 166 enables coupling of the coupling mechanism 140 (and the image recording assembly 142) to the blade 30.

Figure 20:
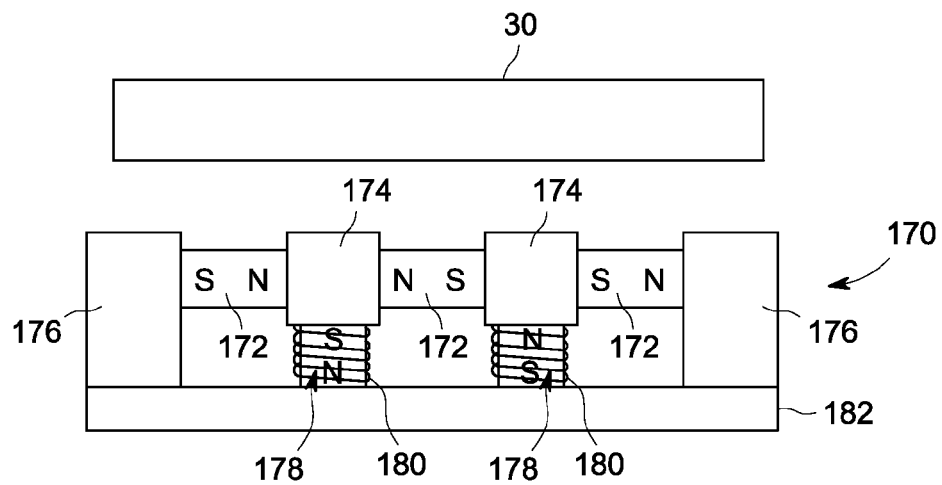
FIGS. 20 and 21 are side schematic views of an electro-permanent magnet coupling mechanism of an image recording assembly in accordance with an embodiment of the present invention.
Figure 21:
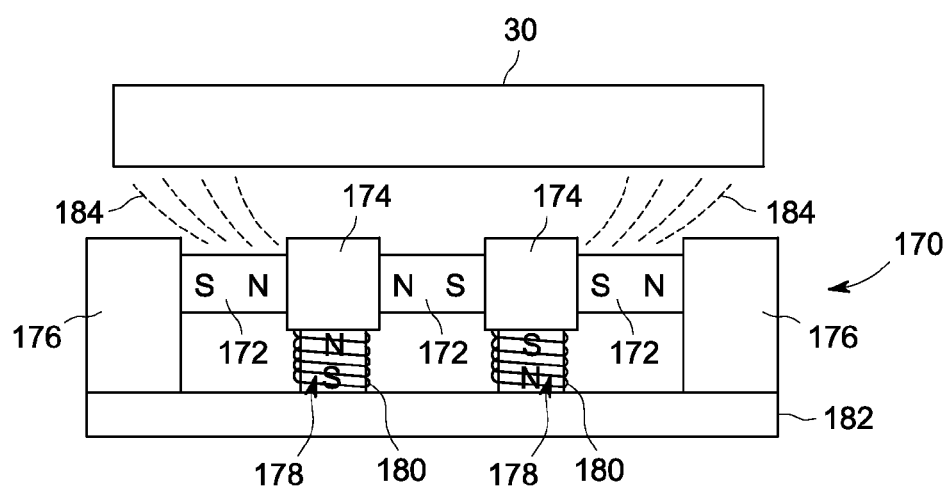

FIGS. 20 and 21 depict front schematic views of an electro-permanent magnet coupling mechanism 170 in accordance with an embodiment of the present invention. The electro-permanent magnet coupling mechanism 170 may include a plurality of primary permanent magnets 172 separated by in-blocks 174. Additionally, the electro-permanent magnet coupling mechanism 170 may include end-blocks 176 at each end of the mechanism 170. As also shown in FIG. 20, the electro-permanent magnet coupling mechanism 170 may include secondary magnets 178 surrounded by coils 180. The polarity of the secondary magnets 178 may be switched by powering the coils 180. Additionally, the end-blocks 176 and the secondary magnets 178 may be supported by a magnetic plate 182.

As shown in FIG. 20, in the "OFF" position the primary magnets 172 and secondary magnets 178 are oriented such that the magnetic field is contained in the coupling mechanism 170 and the coupling mechanism 170 does not produce a magnetic field toward the blade 30. The primary magnets 172 are oriented such that the same polarity is oriented towards the in-blocks 172, and the secondary magnets 178 are oriented such that the opposite polarity of each pair of primary magnets 172 is oriented towards the in-blocks 174.

To activate the coupling mechanism 170 to the "ON" position, the polarities of the secondary magnets 178 may be reversed by powering the coils 180 around the secondary magnets 178. As shown in FIG. 21, by reversing the polarities of the secondary magnets 178, a magnetic field 184 may be exerted external to the coupling mechanism 170 towards the blade 30. After reversing polarity of the secondary magnets 178, each in-block 174 is surrounded by the same polarity, i.e., one in-block is surrounded by the north poles of the magnets 172 and 178 and the other in-block is surrounded by the south poles of the magnets 172 and 178. Thus, the coupling mechanism 170 may produce a magnetic field on the blade 30 to couple the mechanism 170 to the blade 30.

Figure 22:
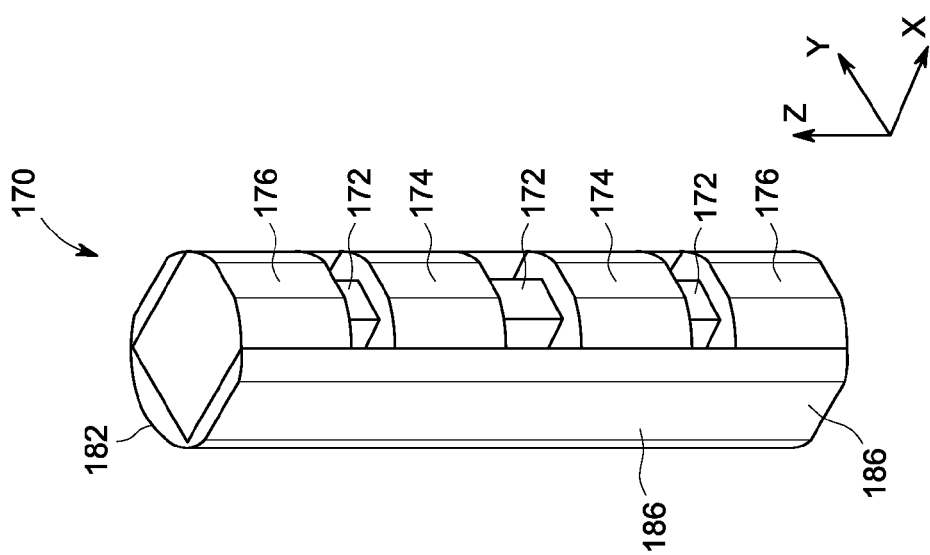

FIG. 22 depicts a perspective view of the electro-permanent magnet coupling mechanism 170 in accordance with an embodiment of the present invention. As noted above, the electro-permanent magnet coupling mechanism 170 may include a plurality of permanent magnets 172 separated by in-blocks 174. Additionally, the electro-permanent magnet coupling mechanism 170 may include end-blocks 176 at each end of the mechanism 170. The magnets 176 and blocks 178 and 180 may be retained by a lock plate 186.

Figure 23:
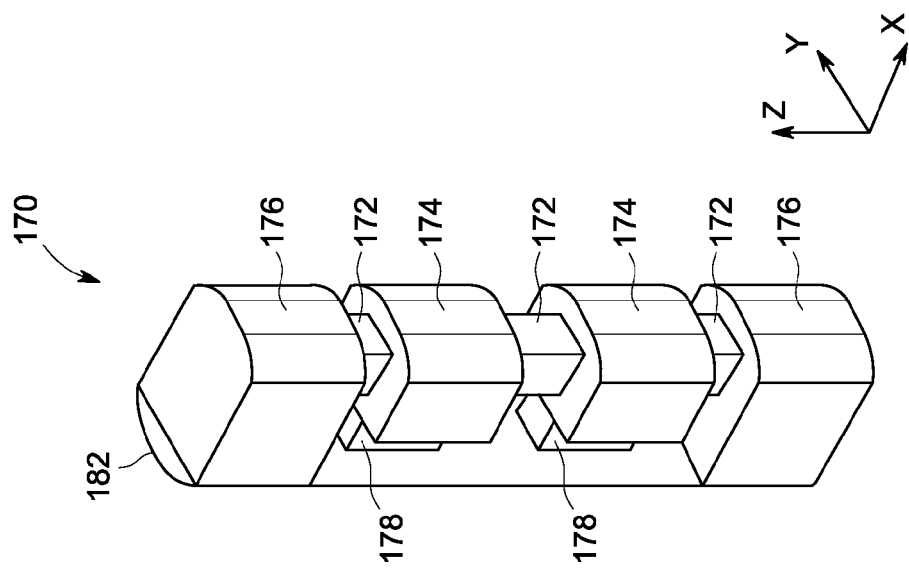
FIGS. 22 and 23 are perspective views of the electro-permanent magnet coupling mechanism of FIGS. 20 and 21 in accordance with an embodiment of the present invention.

FIG. 23 depicts a perspective view of the electro-permanent magnet coupling mechanism 170 with the lock plate 182 removed in accordance with an embodiment of the present invention As shown in FIG. 23, the electro-permanent magnet coupling mechanism 170 may include the secondary permanent magnets 178, The coupling mechanism 170 may also include the coils 180. In some embodiments, the permanent magnets 172 may be NdFeB magnets and the secondary magnets may be AlNiCo magnets. The blocks 174 and 176 may be any suitable ferrous alloy, such as mild steel or low carbon steel.

Figure 24:
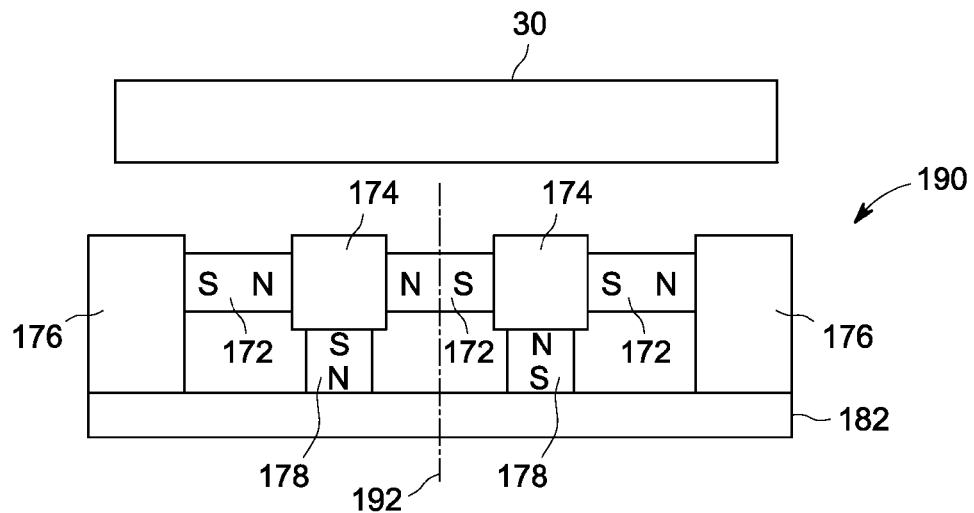
FIGS. 24 and 25 are front schematic views of a magnetic coupling mechanism of an image recording assembly having rotatable magnets in accordance with an embodiment of the present invention.
Figure 25:
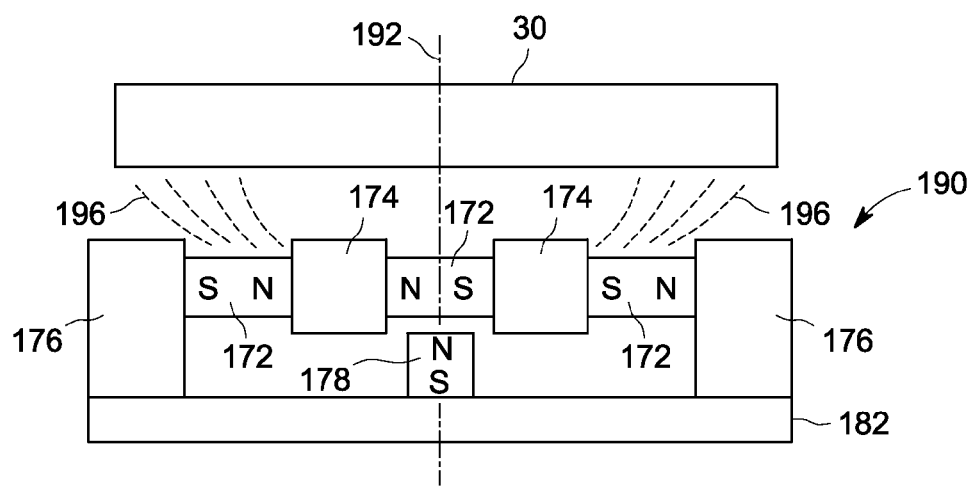

Other embodiments may use a coupling mechanism similar to that described above in FIGS. 20 and 21 but having a mechanical operation to position the secondary magnets 178. For example, the secondary magnets 178 may be mechanically moved, e.g., rotated or translated, to change the location and/or orientation of the poles and produce a magnetic field toward the blade 30. FIGS. 24 and 25 depict side views of a magnetic coupling mechanism 190 having rotatable secondary magnets 178 in accordance with an embodiment of the present invention. Additionally, FIGS. 26 and 27 depict front views of the embodiment shown in FIGS. 25 and 26.

Figure 26:
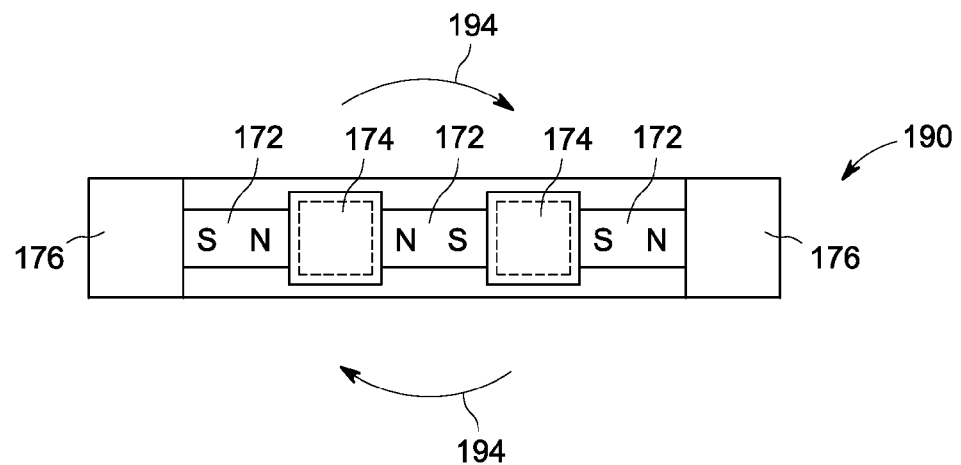
FIGS. 26 and 27 are top schematic views of a magnetic coupling mechanism of FIGS. 24 and 25 in accordance with an embodiment of the present invention.

As shown in FIGS. 24 and 26, in the "OFF" position the secondary magnets 178 are positioned as described above, such that a magnetic field is contained in the coupling mechanism 190, and the coupling mechanism 190 does not exert a magnetic field toward the blade 30. The primary magnets 172 on either side of the in-blocks 174 are oriented such that the same polarity is oriented towards the in-blocks 174, and the secondary magnets 178 are positioned such that the opposite polarity of each pair of primary magnets 172 is oriented towards the in-blocks 174.

Figure 27:
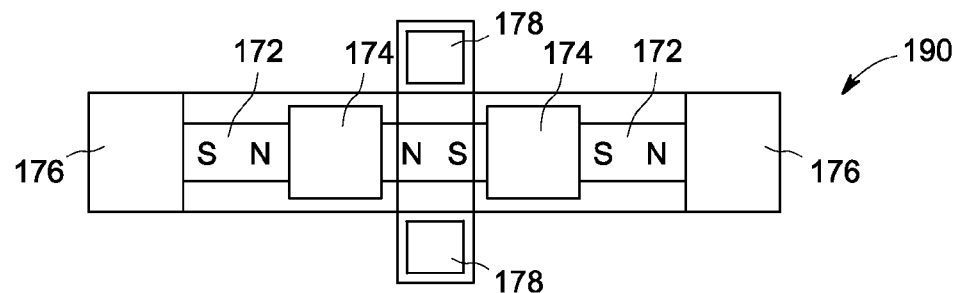

As shown in FIGS. 24 and 27, the secondary magnets 178 may be rotated around axis 192, such as in the direction indicated by arrows 194, to activate the coupling mechanism 190 to the "ON" position. In this position, a magnetic field 196 may be exerted outside of the coupling mechanism 190 towards the blade 30. Each in-block 174 is surrounded by the same polarity, i.e., one in-block is surrounded by the north poles of the magnets 172 and the other in-block is surrounded by the south poles of the magnets 172. Thus, the coupling mechanism 190 may produce an external magnetic field toward the blade 30 to secure the mechanism 190 to the blade 30.

Figure 28:
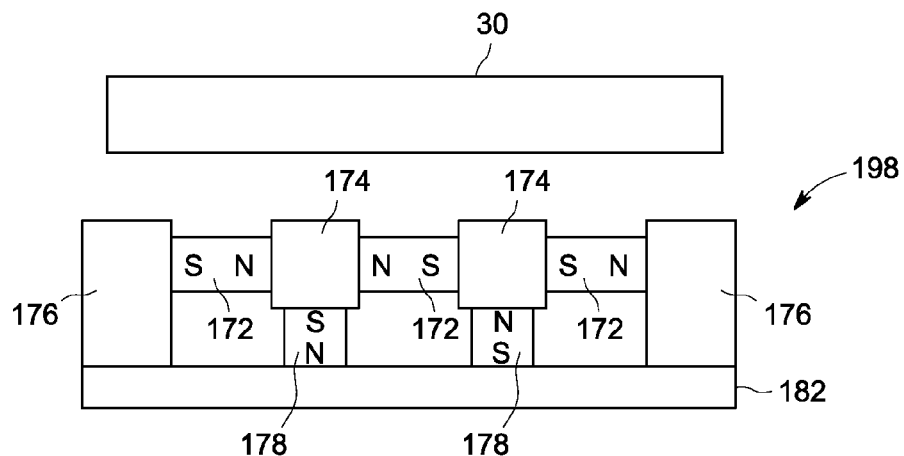
FIGS. 28 and 29 are front schematic views of a magnetic coupling mechanism of an image recording assembly having translatable magnets in accordance with an embodiment of the present invention.
Figure 29:
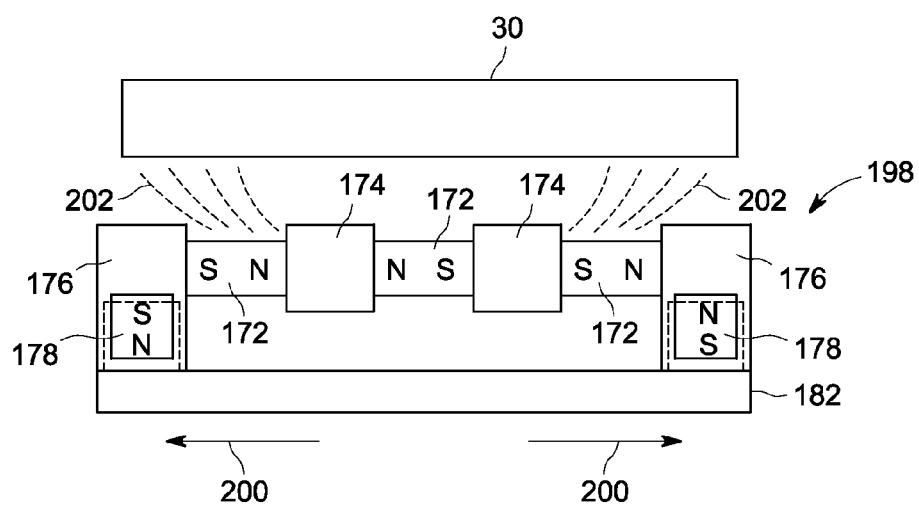
Figure 30:
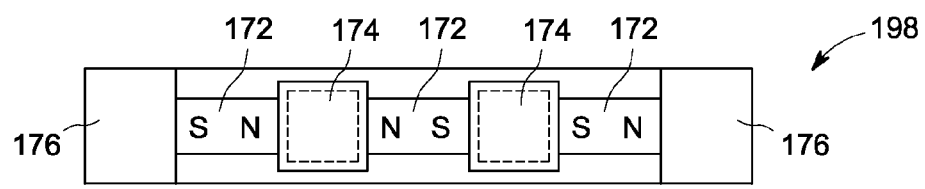
FIGS. 30 and 31 are top schematic views of a magnetic coupling mechanism of FIGS. 28 and 29 in accordance with an embodiment of the present invention.
Figure 31:
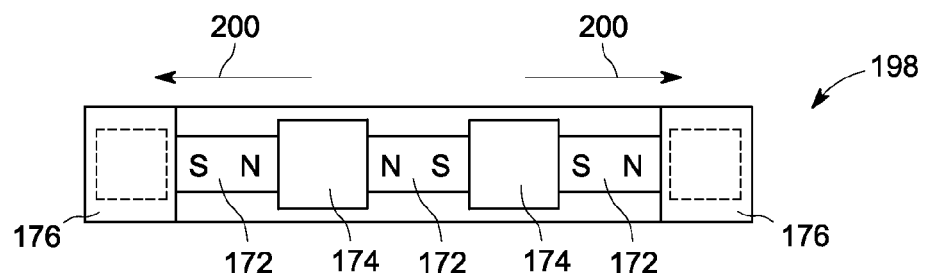

FIGS. 28 and 29 depict front views of an embodiment of a magnetic coupling mechanism 198 having translatable secondary magnets 178. Additionally, FIGS. 30 and 31 depict front views of the embodiment of FIGS. 28 and 29. As shown in FIGS. 28 and 30, in the "OFF" position the secondary magnets 178 are positioned as described above. In this position, that the magnetic field is contained in the coupling mechanism 198. The primary magnets 172 on either side of the in-blocks 174 are oriented such that the same polarity is oriented towards the in-blocks 174, and the secondary magnets 178 are positioned such that the opposite polarity of each pair of primary magnets 172 is oriented towards the in-blocks 174.

As shown in FIGS. 29 and 31, the secondary magnets 172 may be translated in the directions indicated by arrows 200 to activate the coupling mechanism 198 to the "ON" position. In this position, a magnetic field 202 may be exerted outside of the coupling mechanism 198 towards the blade 30. The secondary magnets 178 are translated so that they are removed from interaction with the primary magnets 172. Thus, after repositioning after the secondary magnets 178, each in-block 174 is surrounded by the same polarity, i.e., one in-block is surrounded by the north poles of the magnets 172 and the other in-block is surrounded by the south poles of the magnets 172, enabling production of the magnetic field 202 toward the blade 30.

Figure 32:
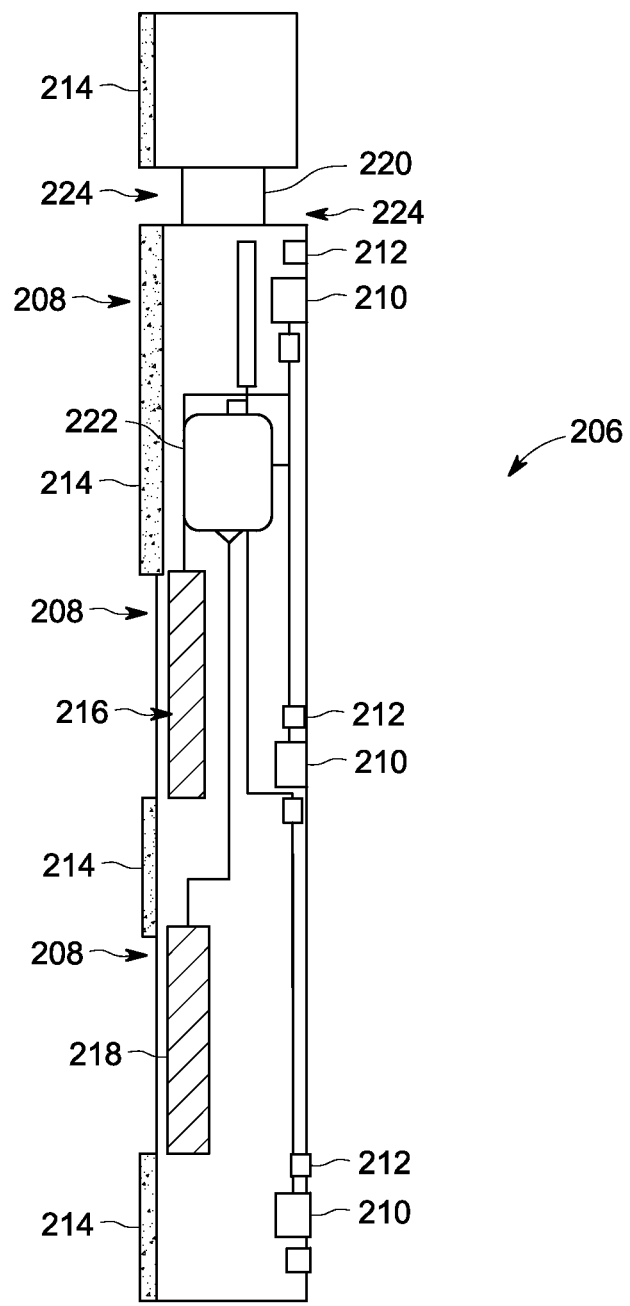
FIG. 32 is a schematic side view of an image recording assembly having multiple coupling mechanisms in accordance with an embodiment of the present invention.

Some embodiments may include any one of, or combination of, the coupling mechanisms described. Further, as noted above, some of the coupling mechanisms may be activated between an "ON" position and an "OFF" position. FIG. 32 depicts a schematic side view of an image recording assembly 206 and multiple coupling mechanisms 208 in accordance with an embodiment of the present invention. As described above, the image recording assembly 206 may include image recording devices 210, e.g., cameras, and light sources 212. The image recording assembly 206 may include other components described above but not shown in FIG. 32, such as processors, power sources, storage devices, etc. The image recording assembly 206 may include multiple coupling mechanisms 208 for coupling the assembly 306 to a blade of a compressor. For example, such coupling mechanisms 208 may include a layer 214 of adhesive, an electro-permanent coupling mechanism 216, as described above in FIGS. 20-23, and a magnetic keepers coupling mechanism 218, as described above in FIGS. 11-16.

To operate those mechanisms 208 that require activation between an "ON" and "OFF" position, the assembly 206 may include a collapsible switch (e.g., spring-activated switch) 220 and a stepper motor 222 activated by the switch 220. The switch 220 and the stepper motor 222 may be powered by the power source (not shown) of the image recording assembly 206. The switch 220 may be manipulated by a gripper or other tool used to insert the image recording assembly 206, such as through recessed portions 224.

To activate the coupling mechanisms 202, the switch 220 may be operated to send power to components of the image recording assembly 206. As mentioned above, the switch 220 may also activate the image recording devices 210, light sources 212, or any other component of the image recording assembly 206. For example, operation of the switch 220 may provide power to the coils of the electro-permanent coupling mechanism 216, as described above in FIGS. 20 and 21. Additionally, operation of the switch 220 may operate the stepper motor 222 to rotate the magnets of the magnetic keepers coupling mechanism 218, as described above in FIGS. 13 and 14. Further, the adhesive layer 214 may provide additional coupling to the blade 30 before, during, and/or after operation of the switch 220. In this manner, multiple coupling mechanisms 208 may be used in a single image recording assembly 206.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for recording images of a stator vane of a compressor of a gas turbine engine, comprising:
   a first subassembly comprising:
      a first image recording device coupled to a first printed circuit board (PCB);
      one or more memories coupled to the PCB; and
      a first processor coupled to the PCB,
   wherein the first subassembly is coupled to an attachment mechanism to form an image recording assembly,
   wherein the attachment mechanism comprises a magnet that when activated is configured to directly secure the image recording assembly to a rotor blade of the compressor of the gas turbine engine.

2. The system of claim 1, comprising a second subassembly, wherein the second subassembly comprises:
   a second image recording device coupled to a second PCB;
   a second one or more memories coupled to the second PCB; and
   a second processor coupled to the second PCB,
   wherein the second subassembly is coupled to the attachment mechanism.

3. The system of claim 1, comprising a third subassembly, wherein the third subassembly comprises:
   a third image recording device coupled to a third PCB;
   a third one or more memories coupled to the third PCB; and
   a third processor coupled to the third PCB,
   wherein the third subassembly is coupled to the attachment mechanism.

4. The system of claim 1, wherein the attachment mechanism comprises adhesive.

5. The system of claim 1, wherein the image recording assembly comprises a switch configured to activate one or both of the image recording device or the attachment mechanism.

6. The system of claim 5, wherein the switch comprises a collapsible switch configured to turn the image recording device either ON or OFF.

7. A system for recording images of a stator vane of a compressor of a gas turbine engine, comprising:
   a first subassembly comprising:
      an image recording device for recording images of the stator vane of a compressor of the gas turbine engine, wherein the image recording device is coupled to a first printed circuit board (PCB) and the PCB is further coupled to one or more memories and a processor;
   and
   a mechanism configured to directly secure the image recording assembly to a rotor blade of the compressor of the gas turbine engine using one or more magnets.

8. The system of claim 7, comprising a coating on a surface of a housing of the mechanism.

9. The system of claim 7, wherein the mechanism comprises an array of magnets and one or more keeper magnets.

10. The system of claim 7, wherein the mechanism comprises a Halbach array of magnets.

11. The system of claim 10, comprising a magnetic keeper on one side of the array.

12. The system of claim 7, wherein the mechanism comprises an electro-permanent magnet array.

13. A method for operating an image recording assembly for recording images of a stator vane of a compressor of a gas turbine engine, comprising:
   inserting an image recording assembly into a compressor housing of the gas turbine engine;
   activating an image recording device of the image recording assembly; and
   activating a magnetic mechanism to directly secure the image recording assembly to a rotor blade of the compressor of the gas turbine engine
   wherein the image recording assembly is coupled to a first printed circuit board (PCB) and the PCB is further coupled to one or more memories and a processor.

14. The method of claim 13, wherein activating the magnetic mechanism comprises powering coils of the magnetic mechanism.

15. The method of claim 13, wherein activating the magnetic mechanism comprises rotating magnets of the magnetic mechanism.

16. The method of claim 13, comprising operating a switch of the image recording assembly to activate one or both of the image recording device or the magnetic mechanism.

17. The method of claim 16, wherein activating the switch of the image recording assembly comprises operating the switch to turn the image recording device either ON or OFF.

18. The method of claim 13, comprising operating a motor to activate the magnetic mechanism.

19. The method of claim 13, comprising coupling the image recording assembly to the rotor blade via an adhesive layer on a housing of the image recording assembly.

* * * * *